(12) United States Patent
Zhou et al.

(10) Patent No.: US 10,883,054 B2
(45) Date of Patent: Jan. 5, 2021

(54) REMOVING CONTAMINANTS FROM CRUDE OIL

(71) Applicant: BP Corporation North America Inc., Houston, TX (US)

(72) Inventors: Chengxiang Zhou, Naperville, IL (US); Ming Wei, Bolingbrook, IL (US); Jason English, Aurora, IL (US); Craig Hackett, Aurora, IL (US)

(73) Assignee: BP Corporation North America Inc., Houston, TX (US)

( * ) Notice: Subject to any disclaimer, the term of this patent is extended or adjusted under 35 U.S.C. 154(b) by 4 days.

(21) Appl. No.: 15/703,179

(22) Filed: Sep. 13, 2017

(65) Prior Publication Data
US 2018/0079969 A1 Mar. 22, 2018

Related U.S. Application Data

(60) Provisional application No. 62/398,043, filed on Sep. 22, 2016.

(51) Int. Cl.
*C10G 17/04* (2006.01)
*C10G 31/08* (2006.01)
(Continued)

(52) U.S. Cl.
CPC .............. *C10G 17/04* (2013.01); *C10G 17/00* (2013.01); *C10G 17/06* (2013.01); *C10G 21/06* (2013.01);
(Continued)

(58) Field of Classification Search
CPC ........ C10G 17/04; C10G 21/06; C10G 17/00; C10G 33/00; C10G 31/08; C10G 17/06;
(Continued)

(56) References Cited

U.S. PATENT DOCUMENTS 5,656,152 A    8/1997  McLaughlin et al.
9,434,889 B2 * 9/2016  Subramaniyam ...... C10G 17/02
(Continued)

FOREIGN PATENT DOCUMENTS

WO   WO 2004/020553   3/2004
WO   WO 2007/005298   1/2007
WO   WO 2016/101998   6/2016

OTHER PUBLICATIONS

Garcia et al., "Chemistry and Impacts of Commonly Used Amine-Based H2S Scavengers on Crude Unit Towers and Overhead," NACE International, Paper No. 07571, 2007, pp. 1-13.

*Primary Examiner* — Randy Boyer
*Assistant Examiner* — Juan C Valencia
(74) *Attorney, Agent, or Firm* — McDonnell Boehnen Hulbert & Berghoff LLP (57) ABSTRACT

A method comprises correlating—in a system which comprises a non-aqueous phase comprising a hydrocarbon fluid, and an aqueous phase—partitioning levels of a basic contaminant and/or an acid of interest into the aqueous phase with the pH of the aqueous phase. The partitioning levels of the basic contaminant and the acid of interest, as well as the pH of the aqueous phase, are obtained under conditions which are representative of those used in a partitioning process in which a basic contaminant is removed from a hydrocarbon fluid.
The correlations may be used in a method for selecting an acidic environment for use in a partitioning process, for estimating corrosion risk downstream of a partitioning process, or for controlling a partitioning process.

19 Claims, 10 Drawing Sheets

(51) Int. Cl.
  *C10G 33/00* (2006.01)
  *C10G 17/00* (2006.01)
  *C10G 21/06* (2006.01)
  *C10G 17/06* (2006.01)
  *G01N 33/28* (2006.01)

(52) U.S. Cl.
  CPC ............ *C10G 31/08* (2013.01); *C10G 33/00* (2013.01); *G01N 33/2823* (2013.01); *G01N 33/2876* (2013.01); *C10G 2300/202* (2013.01)

(58) Field of Classification Search
  CPC ......... C10G 2300/202; G01N 33/2823; G01N 33/2876
  See application file for complete search history.

(56) References Cited

U.S. PATENT DOCUMENTS

| | | | |
|---|---|---|---|
| 2006/0211128 A1* | 9/2006 | Johnson | C10G 31/08 436/173 |
| 2013/0185044 A1* | 7/2013 | Chen | G01N 33/2823 703/12 |
| 2014/0214210 A1* | 7/2014 | Prasad | B01D 17/04 700/272 |

* cited by examiner

REMOVING CONTAMINANTS FROM CRUDE OIL

FIELD OF THE INVENTION

The present invention relates to a method for correlating partitioning levels of a basic contaminant and/or an acid of interest from a hydrocarbon fluid with pH. The correlations may be used in a method for selecting an acidic environment for use in a partitioning process in which a basic contaminant is partitioned from a hydrocarbon fluid into an aqueous phase. The present invention is of particular use in crude oil desalting operations, since it enables basic contaminants, such as ammonia, organic amines and metal salts, to be removed during a desalting operation without unnecessary over-acidification of the crude oil.

BACKGROUND OF THE INVENTION

Crude oil contains a number of contaminants which are desirably removed before the crude oil is processed. Amines are a common unwanted contaminant.

Amines may make their way into a crude oil for a number of reasons. One common reason is due to the use of nitrogen-containing compounds in removing hydrogen sulfide from crude oil during its extraction and/or transportation to the refinery. Nitrogen-containing compounds which are used for this purpose include triazines, in particular monomethylamine triazine (MMA-triazine) and monoethanolamine triazine (MEA-triazine) which react with hydrogen sulfide to given dithiazine compounds and the free amines, i.e. MMA and MEA, respectively.

Other unwanted contaminants include ammonia and metal salts, such as calcium salts, and organic acids, such as naphthenic acids.

Since these contaminants can cause corrosion and fouling in refinery process equipment, it is highly desirable, and economical, to reduce the content of contaminants in a crude oil to low levels in an oil refinery. The effective removal of unwanted contaminants from crude oil is therefore a critical task.

Many contaminants, such as amines, organic acids and metal salts are removed from crude oil by partitioning into an aqueous phase, for instance as part of a desalting process. In typical desalting processes, crude oils are mixed with wash water before they are passed to the desalting unit. Once introduced into the desalting unit, a desalted crude oil phase and an aqueous phase form. The aqueous phase contains water (that which was present in the extracted crude oil, as well as water that has been added to the hydrocarbon stream during processing, such as wash water) and contaminants. A rag layer separates the two phases. The rag layer is a mixture of the aqueous phase and the desalted crude oil phase.

A desalted crude oil stream and an aqueous stream are withdrawn from the desalter through separate lines. The streams are typically withdrawn at points in the desalter which are a distance from the rag layer so as to minimise the presence of any aqueous components in the desalted crude oil stream and vice versa.

In order to encourage partitioning of basic contaminants such as amines and metal salts, the pH of the aqueous phase may be lowered. However, acids that are added to the wash water to lower the pH may themselves partition into the crude oil phase. This is particularly the case at low pH values. Movement of the acids into the crude oil phase in this way can itself lead to problems with refinery apparatus downstream of the desalter. Accordingly, there is a need for a method for partitioning contaminants in a crude oil into an aqueous phase whilst minimising over-acidification of the crude oil. In particular, there is a need for a method for identifying the optimum pH for contaminant partitioning whilst minimising acid carryover for a given pair of basic contaminant and acid.

WO 2004/020553 discloses acidic compositions for removing metals and/or amines, whilst minimising oil carry under, in a refinery desalting process. Preferred compositions comprise, in addition to acidifiers, corrosion inhibitors, demulsifiers, pH adjusters, metal chelants, scale inhibitors and hydrocarbon solvents. Accordingly, it can be seen that the compositions disclosed in WO 2004/020553 are designed as finely tuned additive packages for use in commercial desalting processes.

Water-soluble hydroxyacids are used as an acidifier in WO 2004/020553 in place of commodity acids such as acetic acid, since these hydroxyacids are believed to exhibit lower levels of partitioning into the oil during the refinery desalting process. However, the use of specific water-soluble hydroxyacids in a commercial desalting operation can turn out to be expensive and restricting, e.g. as compared to methods in which commodity acids may be used.

The compositions disclosed in WO 2004/020553 also comprise a mineral acid in an amount sufficient to reduce the pH of the wash water to 6 or below. Whilst a lower pH is generally believed to favour movement of metals and/or amines into the aqueous phase, it has now been found that the elevated temperature and/or pressure that is typically used in a commercial desalter may have a significant effect on pH and thus the partitioning of both contaminants and acids between the aqueous and non-aqueous phases. Accordingly, the use of correlations between ambient pH and partitioning in selecting conditions for a commercial desalting process may be of limited benefit.

Accordingly, there remains a need for further methods for removing contaminants from a crude oil.

SUMMARY OF THE INVENTION

The present invention is based on the discovery that the proportion of basic contaminant (e.g. ammonia, organic amine or metal salt contaminant) that is partitioned into the aqueous phase is strongly dependent on the pH of the aqueous phase at process conditions, which may differ significantly from the pH of the aqueous phase measured under ambient conditions. The partitioning of an acid has also been found to be strongly dependent on the pH of the aqueous phase at process conditions. The correlations between partitioning levels and process pH are largely independent of the nature of the acid or base that is used to control the pH, with lower pH favouring successful contaminant partitioning into the aqueous phase, and higher pH favouring successful partitioning of the acids into the aqueous phase. By carefully selecting an acidic environment, contaminants in a crude oil may therefore be effectively partitioned into an aqueous phase whilst minimising over-acidification. This optimisation of a partitioning process forms the basis of the present invention.

Accordingly, the present invention provides a method comprising:

(a) correlating—in a system which comprises a basic contaminant, a non-aqueous phase comprising a hydrocarbon fluid, and an aqueous phase—the partitioning level of the basic contaminant into the aqueous phase with the pH of the aqueous phase; or (b) correlating—in a system which comprises an acid of interest, a non-aqueous phase comprising a hydrocarbon fluid, and an aqueous phase—the partitioning level of the acid of interest into the aqueous phase with the pH of the aqueous phase;

wherein the partitioning levels of the basic contaminant and the acid of interest, as well as the pH of the aqueous phase, have been obtained under conditions which are representative of those used in a partitioning process in which a basic contaminant is removed from a hydrocarbon fluid.

The present invention further provides a method for selecting an acidic environment for use in a partitioning process in which a basic contaminant is removed from a hydrocarbon fluid, said method comprising:
(c) selecting an acidic environment for use in the partitioning process based on correlations determined using methods disclosed herein.

Also provided is a method for controlling a partitioning process in which a basic contaminant is removed from a hydrocarbon fluid, said method comprising:
(i) selecting an acidic environment using the methods disclosed herein; and
(ii) operating the partitioning process with the acidic environment selected in (i).

A method for estimating corrosion risk downstream of a partitioning process in which a basic contaminant is removed from a hydrocarbon fluid is also provided, said method comprising estimating the corrosion risk based on correlations determined using the methods disclosed herein.

The present invention also provides a database comprising:
(a) a correlation—in a system which comprises a basic contaminant, a non-aqueous phase comprising a hydrocarbon fluid, and an aqueous phase—between the partitioning level of the basic contaminant into the aqueous phase with the pH of the aqueous phase; or
(b) a correlation—in a system which comprises an acid of interest, a non-aqueous phase comprising a hydrocarbon fluid, and an aqueous phase—between the partitioning level of the acid of interest into the aqueous phase with the pH of the aqueous phase;

wherein the partitioning levels of the basic contaminant and the acid of interest, as well as the pH of the aqueous phase, have been obtained under conditions which are representative of those used in a partitioning process in which a basic contaminant is removed from a hydrocarbon fluid.

The database may be used in a method for selecting an acidic environment for a partitioning process in which a basic contaminant is removed from a hydrocarbon fluid, for estimating corrosion risk downstream of a partitioning process in which a basic contaminant is removed from a hydrocarbon fluid, or for controlling a partitioning process in which a basic contaminant is removed from a hydrocarbon fluid.

DETAILED DESCRIPTION OF THE INVENTION

The present invention provides a method for correlating—in a system which comprises a non-aqueous phase comprising a hydrocarbon fluid, and an aqueous phase—partitioning levels of a basic contaminant and/or an acid of interest with the pH of the aqueous phase. Preferably, correlations are obtained for both a basic contaminant and an acid of interest.

It will be appreciated that species other than the basic contaminant and the acid of interest may be present in the systems, including further acids, bases and salts (e.g. those species that may typically be present in crude oil streams in a refinery).

Contaminant

The basic contaminant may be selected from ammonia, organic amines, salts, and combinations thereof. These contaminants are typically found in hydrocarbon fluids such as crude oil or other refinery feedstocks. Optimising the removal of such contaminants is highly desirable in industrial partitioning processes, such as a desalting process in a refinery.

Organic amine contaminants may be selected from monomethylamine, ammonia, and monoethanolamine, diethanolamine, ethylamine, diglycolamine, methyldiethanolamine, dimethylethanolamine, trimethylamine, propylamine, morpholine, dimethylisopropanolamine, diethylamine, 3-methoxypropylamine, N-methylmorpholine, 2-butylamine, N-ethylmorpholine, butylamine, cyclohexylamine, ethylenediamine, and combinations thereof. These amine contaminants are often found in hydrocarbons fluids such as crude oil and are implicated in problems with corrosion and fouling downstream in a refinery. However it will be appreciated that these amine contaminants are merely exemplary and a wide range of amine contaminants may be found in the hydrocarbon fluid.

Salt contaminants may be selected from metal salts and combinations thereof, with the metal typically being a group 1 or group 2 metal. Preferably, the contaminant is selected from sodium salts, potassium salts, calcium salts, iron salts and combinations thereof. These salt contaminants, e.g. in their chloride form, are often found in hydrocarbons fluids such as crude oil.

Preferably, the basic contaminant is selected from monomethylamine, monoethanolamine, ammonia and combinations thereof.

Since crude oil will generally comprise ammonia, organic amines and basic salts then, in some embodiments, the method of the present invention may be used for selecting an acidic environment for use in a partitioning process in which ammonia, at least one organic amine and at least one basic salt are removed from crude oil.

The system may comprise the basic contaminant in an amount of from 0.1 to 300, preferably from 0.5 to 100, and more preferably from 1 to 50 ppm by weight.

Acid of Interest

Any acid may be used as the acid of interest. The acid of interest may be a single acid or a mixture of acids.

In preferred embodiments, the method of the present invention comprises repeating step (b) for a plurality of acids of interest. This enables correlations for a number of acids of interest to be prepared. For instance, the method of the present invention may comprise repeating step (b) for at least 3 acids of interest, preferably at least 4 acids of interest, and more preferably at least 6 acids of interest.

In some embodiments, the acid of interest, or each of the acids of interest, is selected from hydrochloric acid, acetic acid, glycolic acid, citric acid, malic acid, maleic acid, hydrogen sulfide, carbon dioxide, and mixtures thereof. Other acids, such as other carboxylic acids, may also be used.

It will be appreciated that hydrogen sulfide and carbon dioxide are acidic in the aqueous phase of the system. Hydrogen sulfide and carbon dioxide are contaminants that are commonly found in crude oil. They are generally not desired in the system and so, whilst they may be present, they will generally not be added as an acidifying agent to the system.

Hydrocarbon Fluid

The hydrocarbon fluid is preferably a refinery feedstock, such as a crude oil. Crude oils contain the basic contaminants discussed herein, such as ammonia, organic amines and salts. Accordingly, when a crude oil is used, the basic contaminants may be introduced into the system via the crude oil. In these embodiments, the partitioning process is preferably a desalting process, e.g. in a refinery.

Correlating Partitioning Levels and pH

Steps (a) and (b) of the method of the present invention involve correlating partitioning levels of a basic contaminant and an acid of interest, respectively, into the aqueous phase with the pi of the aqueous phase.

The method may comprise obtaining the partitioning levels of the basic contaminant into the aqueous phase at a plurality of pH levels under conditions which are representative of those used in the partitioning process. The method may also comprise obtaining the partitioning levels of the acid of interest into the aqueous phase at a plurality of pH levels under conditions which are representative of those used in the partitioning process. In embodiments, the method comprises obtaining the partitioning levels of the basic contaminant and the acid of interest into the aqueous phase at a plurality of pH levels under conditions which are representative of those used in the partitioning process. It will be appreciated that the results that are obtained will be used for the correlations in steps (a) and (b) of the method.

The method may further comprise providing the system which comprises the contaminant, a non-aqueous phase comprising a hydrocarbon fluid, and an aqueous phase (i.e. the system referred to in step (a) of the method), e.g. by contacting a hydrocarbon fluid comprising the contaminant with water. The method may also comprise providing the system which comprises an acid of interest, a non-aqueous phase comprising a hydrocarbon fluid, and an aqueous phase (i.e. the system referred to in step (b) of the method), e.g. by contacting a hydrocarbon fluid with an aqueous acid solution.

The systems referred to in steps (a) and (b) of the method will each generally comprise water in an amount of from 0.5 to 20%, preferably from 1 to 15%, and more preferably from 3 to 10% by weight of the system.

The systems are preferably subjected to mixing before the partitioning levels of the acid of interest and the contaminant are obtained. This facilitates partitioning of contaminants that are originally present in the non-aqueous phase (e.g. as part of a crude oil) into the aqueous phase. Methods for mixing are known in the art.

The partitioning levels of each of the basic contaminant and the acid of interest into the aqueous phase may be calculated as follows:

$$\text{Partitioning level (\% by weight)} = \frac{\text{Amount in aqueous phase (by weight)}}{\text{Total amount in system (by weight)}}$$

The amount of contaminant and acid of interest may be obtained by direct measurement, modelling, or combinations thereof. Ion chromatography (IC) may be used to directly measure the amount of contaminant and acid of interest, e.g. by sampling of the aqueous phase, the non-aqueous phase, the hydrocarbon fluid before it is contacted with water, and/or the water before it is contacted with the hydrocarbon fluid. Known electrolyte modelling techniques may also be used.

In order to identify the optimum pH for partitioning, the partitioning levels of the acid of interest and the contaminant may be obtained at a plurality of pH levels between 1 and 10, preferably between 2 and 8, and more preferably between 3 and 7. In preferred embodiments, the partitioning levels may be measured at a pH of less than 4, at a pH of greater than 6 and at one or more pH levels therebetween. These pH levels are generally preferred for partitioning processes for practical reasons (e.g. corrosion control); it will be appreciated that the preferred pH levels for partitioning will vary based on the chemical nature of the particular basic contaminant and acid of interest used.

The partitioning levels are preferably obtained at greater than 4, more preferably greater than 6, and still more preferably greater than 10 pH levels.

In preferred embodiments, the pH of the aqueous phase is varied by modifying the amount of acid that is present in the systems referred to in steps (a) and (b). The amount of acid in the systems is preferably varied by adding varying amounts of the acid of interest, but may also be varied by adding varying amounts of one or more further acids.

The pH of the aqueous phase may be measured directly or indirectly.

Direct determination of the pH of the aqueous phase involves direct measurement of pH of the aqueous phase under conditions which are representative of those used in the partitioning process, e.g. elevated temperature and pressure. Suitable pH meters for carrying out such measurements are known in the art.

However, direct measurement of pH can be challenging at high temperatures and pressures, with equipment malfunction not uncommon over time. Accordingly, in other embodiments, the pH of the aqueous phase is determined indirectly. For instance, the pH may be estimated using a method which comprises: analysing the aqueous stream to determine the content of different organic and inorganic components (e.g. amines, acids and salts) and, based on the analysis, estimating the pH under different conditions using known electrolyte modelling tools. Other established tools may also be used for estimating the pH.

A crucial aspect of the present invention is that the partitioning levels of the contaminant and the acid of interest, as well as the pH of the aqueous phase, have been obtained (or are measured, in embodiments where this forms part of the method of the present invention) under conditions which are representative of those used in the partitioning process. This is important because the pH of the systems disclosed herein may vary greatly when measured under ambient conditions as compared to process conditions.

In preferred embodiments, the partitioning levels and pH are obtained at a temperature which is representative of (e.g. the same as) that used in the partitioning process, such as a temperature in the range of from 20 to 300° C., preferably from 80 to 150° C., and more preferably from 110 to 140° C.

In preferred embodiments, the partitioning levels and pH are obtained at a pressure which is representative of (e.g. the same as) that used in the partitioning process, such as a pressure in the range of from 100 to 3000 kPa, preferably from 500 to 2500 kPa, and more preferably from 1000 to 2000 kPa.

It will be appreciated that the use of a high temperature is preferably accompanied by the use of a high pressure, as is the case in industrial desalting operations, so that the more volatile components in the systems are substantially maintained in the liquid phase.

Once measurements of partitioning levels across a plurality of pH levels have been obtained, then a correlation between partitioning level and pH may be determined for the contaminant and the acid of interest. A person of skill in the art would be aware of methods for correlating partitioning levels with pH, e.g. using correlation and modelling tools.

In some embodiments, the correlation between partitioning level and pH may be expressed using the following formula:

$$\text{partitioning level (\%)} = ax^6 + bx^5 + cx^4 + dx^3 + ex^2 + fx + g$$

where: x is the pH of the aqueous phase under process conditions; and a to g are constants.

It will be appreciated that the constants a to g will vary for each basic contaminant and acid of interest. The constants may be determined using known polynomial methods.

Selecting an Acidic Environment

In one aspect of the present invention, the correlations determined in steps (a) or (b), and preferably steps (a) and (b), of the method disclosed herein are used for selecting an acidic environment for use in a partitioning process in which the basic contaminant is removed from a hydrocarbon fluid.

Preferably, the step of selecting an acidic environment comprises selecting a pH for the aqueous phase that is present in the partitioning process. In embodiments where correlations are determined for a plurality of acids of interest in step (b), the step of selecting an acidic environment preferably also comprises selecting an acid from the plurality of acids of interest for use in the partitioning process.

The acidic environment is preferably selected because it correlates with a target level of basic contaminant partitioning into the aqueous phase, for instance a target partitioning level of greater than 50%, preferably greater than 70%, and more preferably greater than 90%. Preferably, the selected acidic environment also correlates with a target level of acid of interest partitioning into the aqueous phase, for instance a target partitioning level of greater than 50%, preferably greater than 70%, and more preferably greater than 90%. Though these ranges are preferred, it will be appreciated that the target levels of partitioning for some contaminants and acids of interest may be less than 50%.

Though basic contaminant and acid partitioning levels are the primary and second considerations, respectively, in selecting an acidic environment, other considerations may also be taken into account. These include economic factors (e.g. cost of different acids of interest and volume of acid e.g. required to achieve target pH), logistical factors (e.g. availability and ease of storage of different acids of interest) and process factors (e.g. effect of residual acid of interest in the hydrocarbon fluid downstream of the partitioning process and ease of disposal of aqueous phase into which the acid of interest has been partitioned).

For instance, the step of selecting the acidic environment may comprise: in a first step, limiting the possible acidic environments to those which can provide a target contaminant partitioning level and, in a second step, further limiting the possible acidic environments to those which can provide a target acid of interest partitioning level. The acidic environment may then be selected from the subset of possible acidic environments, e.g. based on economic factors. For instance, where a plurality of acids of interests have been considered, the minimum amount of each acid that would be required to achieve a pH which correlates with a target contaminant partitioning level and a target acid of interest partitioning level may be calculated. The monetary cost of running the partitioning process with each acid of interest could then be calculated, and the cheapest option selected.

Partitioning Process

Once an acidic environment has been selected, it may be used in a partitioning process in which the basic contaminant is removed from a hydrocarbon fluid. Accordingly, a method for controlling a partitioning process comprises: (i) selecting an acidic environment using the methods disclosed herein; and (ii) operating the partitioning process with the acidic environment selected in (i).

The correlation between the partitioning levels and pH will be highly variable for different basic contaminants. Accordingly, it will be understood that the contaminant that is used in the method for selecting the acidic environment is the same as the contaminant which is removed from the hydrocarbon fluid in the method for optimising a partitioning process.

The hydrocarbon fluid that is used in the method of selecting the acidic environment, however, does not necessarily have to be the same as that which used in the method for optimising a partitioning process. However, the use of the same hydrocarbon fluid is highly preferred, since the properties of the hydrocarbon fluid (e.g. origin, API gravity, distillation profile, etc.) can have an effect on the correlation between partitioning levels of the contaminant and acid of interest with the pH of the aqueous phase. Preferred hydrocarbon fluids are those mentioned previously in connection with the method of selecting the acidic environment, with crude oil highly preferred.

In preferred embodiments, the partitioning process is operated at a temperature in the range of from 20 to 300° C., preferably from 80 to 150° C., and more preferably from 110 to 140° C.

In preferred embodiments, the partitioning process is operated at a pressure in the range of from 100 to 3000 kPa, preferably from 500 to 2500 kPa, and more preferably from 1000 to 2000 kPa.

The partitioning process may be a desalting process that is carried out in a desalting unit, e.g. in a refinery. Crude oil is preferably used as the feedstock for the desalting operation.

Any conventional desalting unit may be used in the invention. A desalting unit will typically have an inlet, a hydrocarbon outlet and an aqueous outlet. In the process of the invention, the crude oil (containing the contaminant), and wash-water are introduced into the desalter via the inlet.

Preferably, the crude oil and wash-water are mixed, e.g. by being passed through a mixing valve, to encourage partitioning of the contaminant from the crude oil to the aqueous phase. A non-aqueous phase comprising crude oil is removed from the desalter via the hydrocarbon outlet. An aqueous phase is removed from the desalter via the aqueous outlet.

Wash-water may be added to the crude oil in an amount of from 0.5 to 20%, preferably from 1 to 15%, and more preferably from 3 to 10% by total weight of crude oil and wash-water.

The selected acidic environment (e.g. selected aqueous phase pH or selected acid of interest) may be achieved in the partitioning process by introducing appropriate quantities of acid into the partitioning process, e.g. by acidification of the wash water. Other methods for achieving an aqueous phase having a selected pH include introducing into the partitioning process appropriate quantities of one or more of the following components: bases, $H_2S$ scavengers, calcium removal agents and neutralisers.

In preferred embodiments, the method for controlling the partitioning process comprises, in step (i), selecting a pH for the aqueous phase that is present in the partitioning process. In these embodiments, the method preferably further comprises monitoring the pH of the aqueous phase in the partitioning process at process conditions, and maintaining the pH of the aqueous phase at the selected pH.

The pH of the aqueous phase may be monitored using those methods described above, i.e. by direct or indirect measurement. Preferably, the pH of the aqueous phase is monitored by indirect measurement, e.g. using those methods outlined above. Traditionally, the pH of the aqueous phase in a desalter is either monitored at ambient conditions, which may differ significantly from the pH under process conditions, or is not monitored at all.

In some embodiments, the conditions (e.g. temperature and pressure) in the partitioning process (i.e. in the desalting unit) are also monitored. The compositions of the components in the aqueous phase may also be analysed. This allows variations in the conditions in the partitioning process to be reflected in the indirect measurement of pH.

The pH of the aqueous phase may be maintained by modifying the amount of acid of interest, or other acid, that is introduced into the partitioning process. For instance, the pH may be maintained by varying the degree to which the wash-water is acidified. Other methods include modifying the amount in which of one or more of the following components are introduced into the partitioning process: bases, $H_2S$ scavengers, calcium removal agents and neutralisers. Preferably the pH of the aqueous phase is maintained by modifying the amount of acid and base that is introduced into the partitioning process.

The pH may be maintained within ±0.5 pH units, preferably within ±0.3 pH units, and more preferably within ±0.1 pH units of the pH that was selected for the aqueous phase in step (i). This means that, where a pH of 4.0 has been selected for the acidic environment, the aqueous phase is maintained at a pH of from 3.5 to 4.5, preferably from 3.7 to 4.3, and more preferably from 3.9 to 4.1.

In some embodiments, a closed-loop control system may be used for monitoring and maintaining the pH of the aqueous phase, e.g. where an online pH meter is used with the partitioning process.

The method for controlling the partitioning process may be used to optimise the partitioning process. In some instances, the method optimises the partitioning process by increasing the proportion of contaminant that is removed from the hydrocarbon fluid. Preferably, the method also optimises the partitioning process by reducing the proportion of acid of interest that is present in the non-aqueous stream.

An optimised partitioning process preferably increases the partitioning level of contaminant into the aqueous phase to greater than 50%, preferably greater than 70%, and more preferably greater than 90%. An optimised partitioning process preferably also achieves a partitioning level of acid of interest into the aqueous phase of greater than 50%, preferably greater than 70%, and more preferably greater than 90%.

The method for controlling the partitioning process may also be used optimise refinery processes that are found downstream of the partitioning process and which benefit from an improvement in the partitioning process. For example, the processes described herein may be to reduce corrosion and fouling downstream of the partitioning process.

The correlations obtained using the methods of the present invention may also be used for estimating corrosion risk downstream of the partitioning processes disclosed herein.

Databases of Correlations

The present invention also provides a database which comprises: a correlation—in a system which comprises a basic contaminant, a non-aqueous phase comprising a hydrocarbon fluid, and an aqueous phase—between the partitioning level of the contaminant into the aqueous phase with the pH of the aqueous phase. Preferably, the database comprises correlations for at least 2, preferably at least 4, and more preferably at least 8 basic contaminants.

The database may alternatively comprises a correlation—in a system which comprises an acid of interest, a non-aqueous phase comprising a hydrocarbon fluid, and an aqueous phase—between the partitioning level of the acid of interest into the aqueous phase with the pH of the aqueous phase. The database preferably comprises correlations for at least 2, preferably at least 4, and more preferably at least 8 acids of interest.

The partitioning levels of the basic contaminant and the acid of interest, as well as the pH of the aqueous phase, were obtained under conditions which are representative of those used in the partitioning process.

Preferably, the database comprises at least one correlation between the partitioning level of the basic contaminant into the aqueous phase with the pH of the aqueous phase, and at least one correlation between the partitioning level of the acid of interest into the aqueous phase with the pH of the aqueous phase.

The database may be stored on a computer readable medium, or it may be stored as a cloud database.

The database may be used in carrying out the methods of selecting an acidic environment disclosed herein, so that the partitioning levels of the contaminant and the acid of interest into the aqueous phase at a plurality of process pH levels do not have to be measured and the correlations in steps (a) and (b) can be obtained directly from the database. Thus, the database may be used in a method of selecting an acidic environment for a partitioning process in which a contaminant is removed from a hydrocarbon fluid, the contaminant being an amine or a salt.

The database may also be used in methods disclosed herein for estimating corrosion risk downstream of a partitioning process in which a basic contaminant is removed from a hydrocarbon fluid, or for controlling (e.g. optimising) a partitioning process in which a basic contaminant is removed from a hydrocarbon fluid.

The invention will now be described with reference to the accompanying figures and examples.

EXAMPLES

The following examples describe experiments in which the partitioning levels of basic contaminants and acids into an aqueous phase were measured across a range of pH levels. References to process conditions indicate a temperature of 135° C. and a pressure of 1520 kPa. A crude oil was used having an API gravity of 25.5, and the following distillation profile:

| Volume % | ° C. |
|---|---|
| 0.6 | −1 |
| 3 | 95 |
| 6 | 149 |
| 8 | 175 |
| 13 | 232 |
| 26 | 342 |
| 29 | 369 |
| 46 | 509 |
| 51 | 550 |
| 59 | 585 |
| 64 | 600 |
| 76 | 650 |
| 86 | 700 |
| 93 | 750 |
| 97 | 800 |
| 100 | 1000 |

A water content of approximately 7% by weight of the water-oil mixture was used. pH levels were measured indirectly using an electrolyte modelling package from OLI Systems, Inc.

Figure 1A:
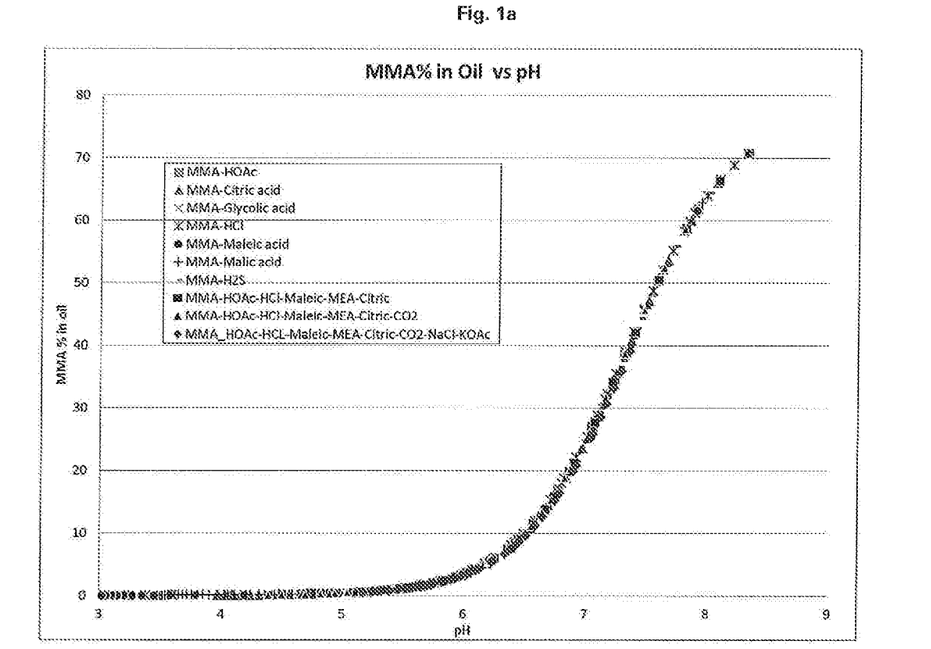
FIGS. 1a-c are graphs depicting the correlation between partitioning levels of different amines with aqueous phase pH measured under process conditions.
Figure 1B:
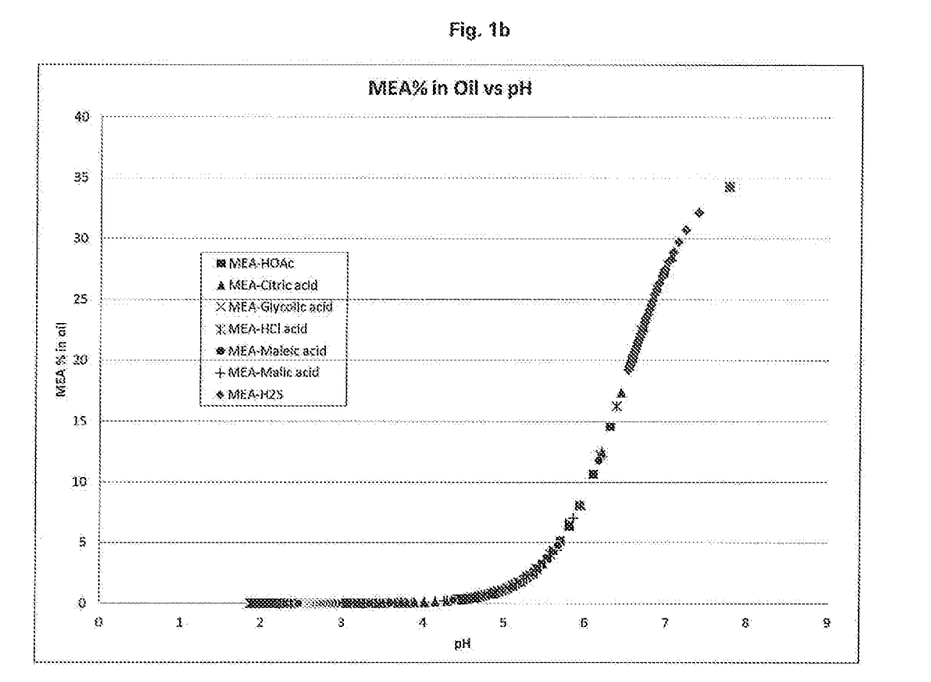
Figure 1C:
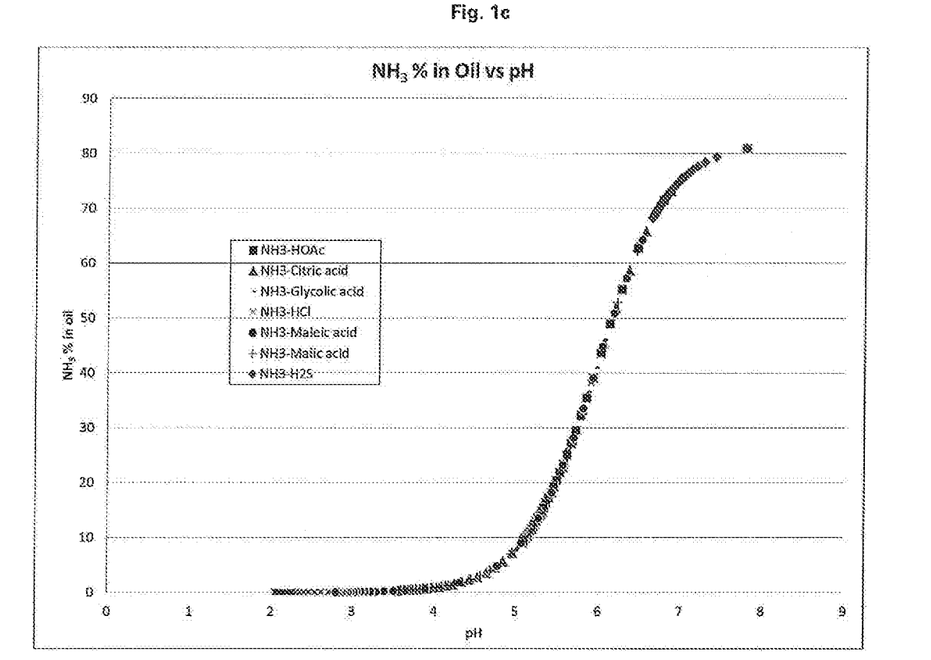
Figure 2A:
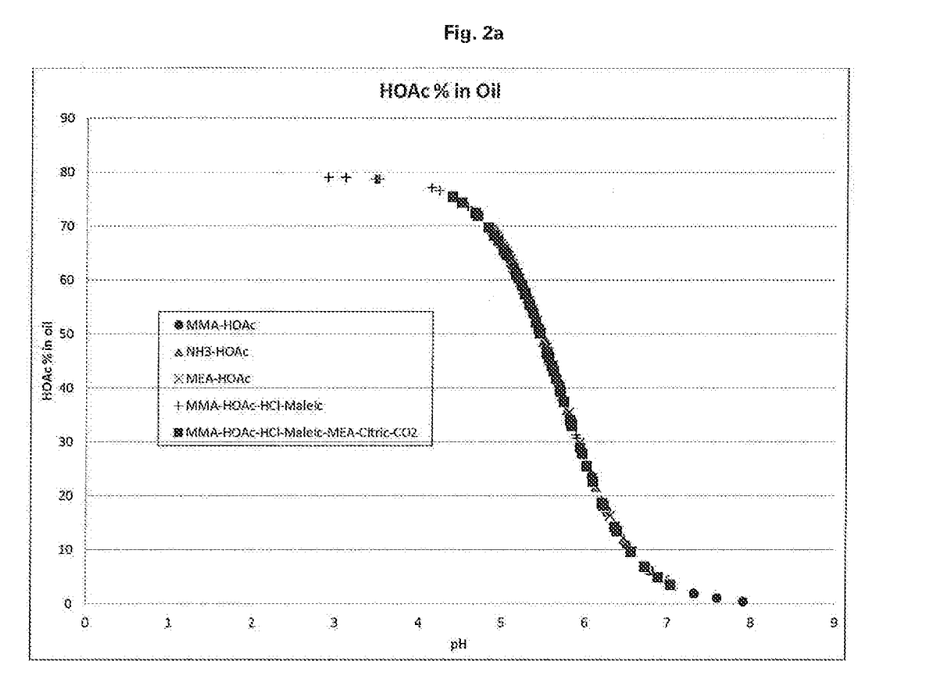
FIGS. 2a-g are graphs depicting the correlation between partitioning levels of different acids with aqueous phase pH measured under process conditions.
Figure 2B:
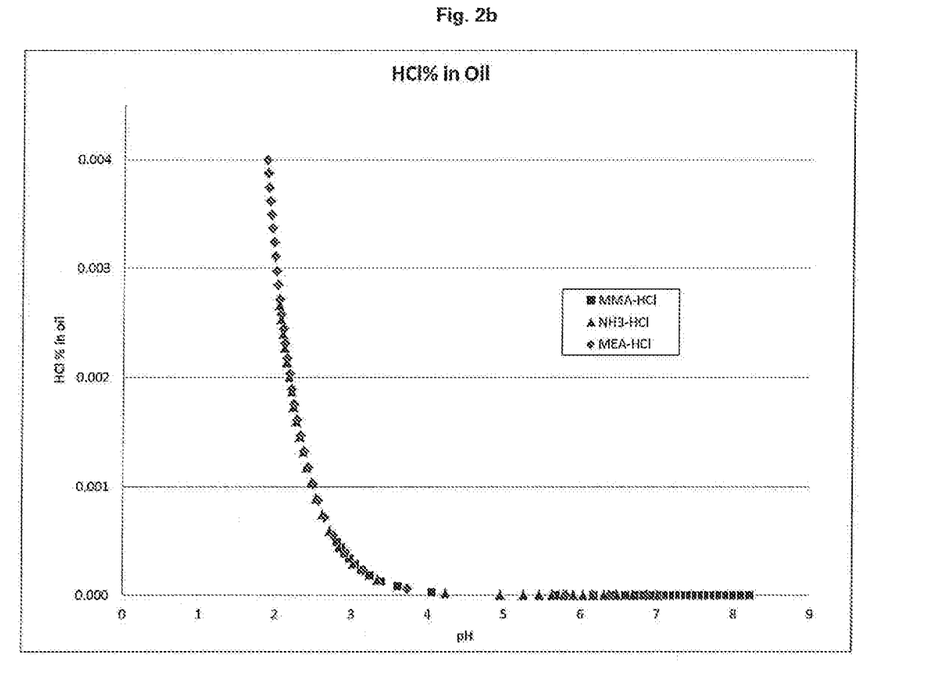
Figure 2C:
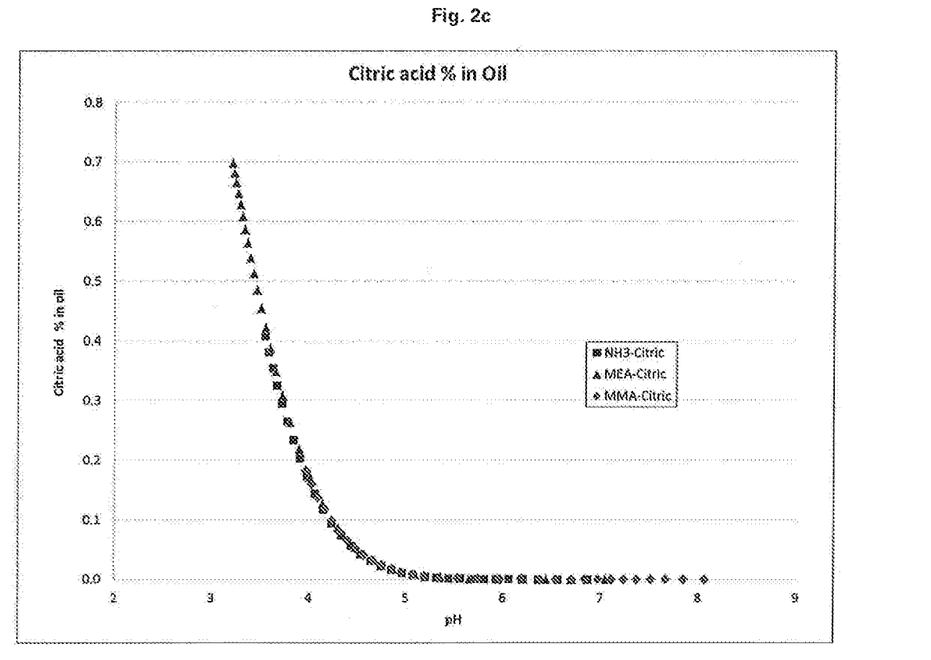
Figure 2D:
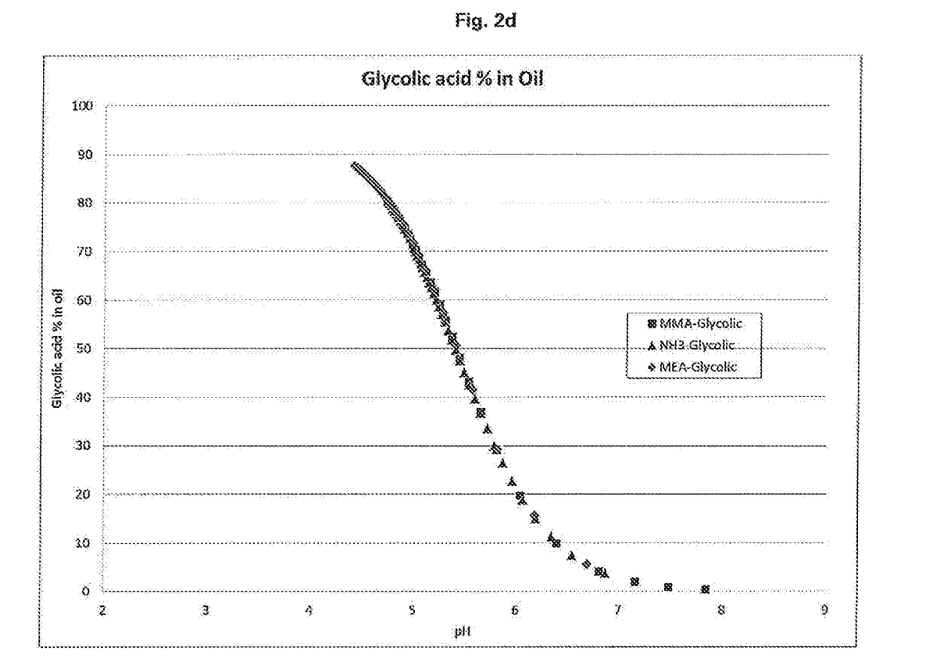
Figure 2E:
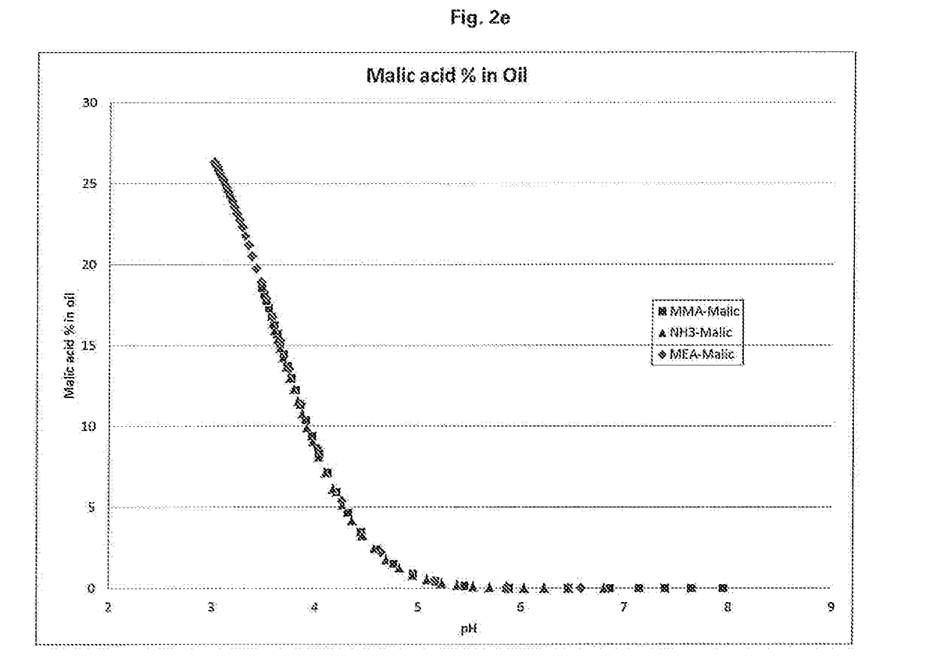
Figure 2F:
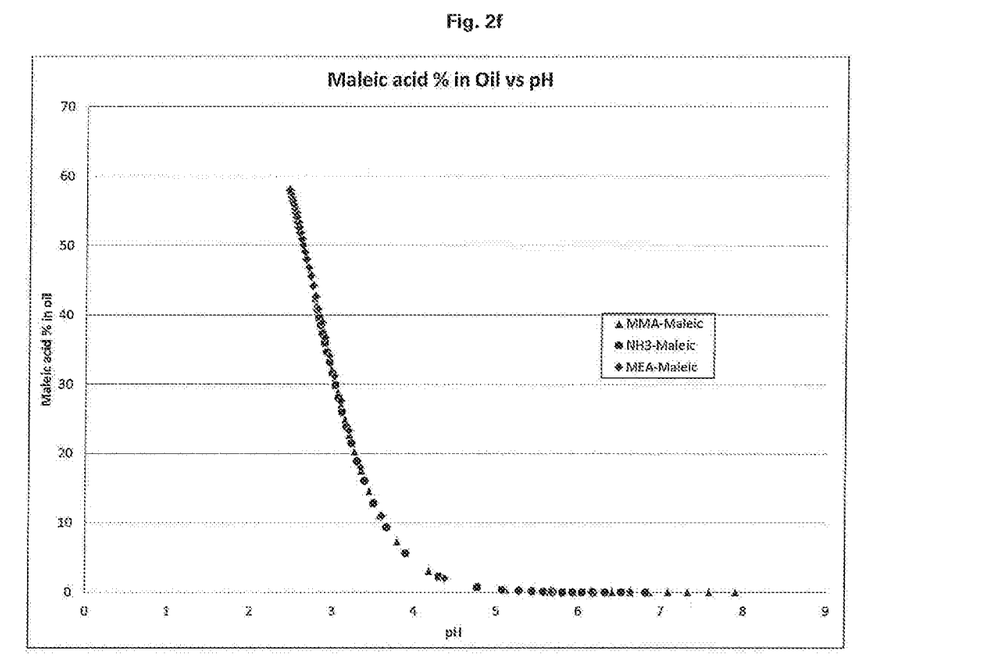
Figure 2G:
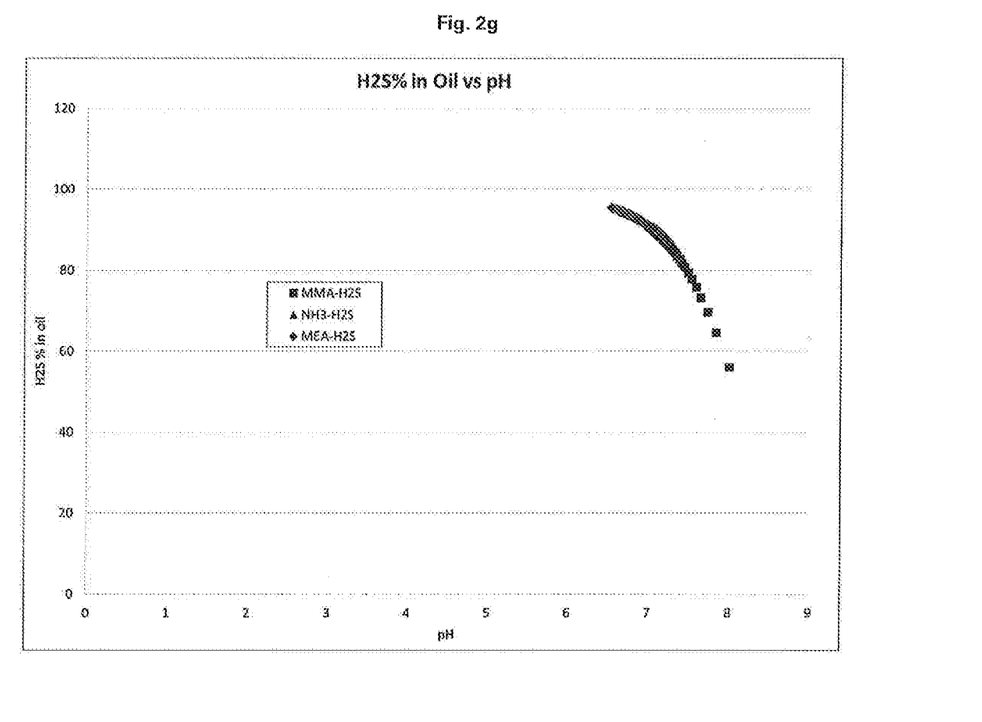
Figure 3A:
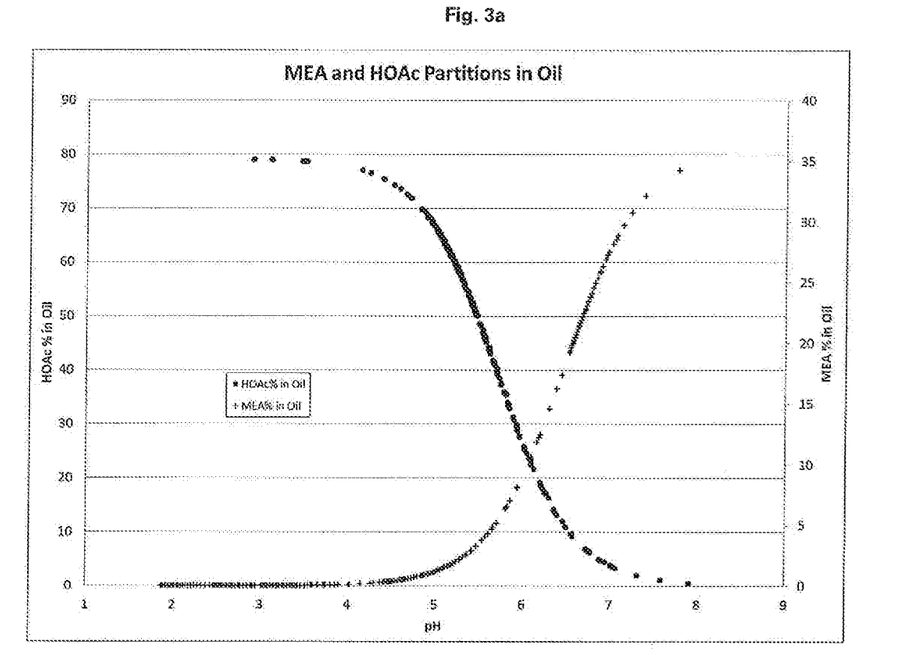
FIGS. 3a-f are graphs depicting the correlation between partitioning levels of monoethanolamine and different acids with aqueous pH measured under process conditions.
Figure 3B:
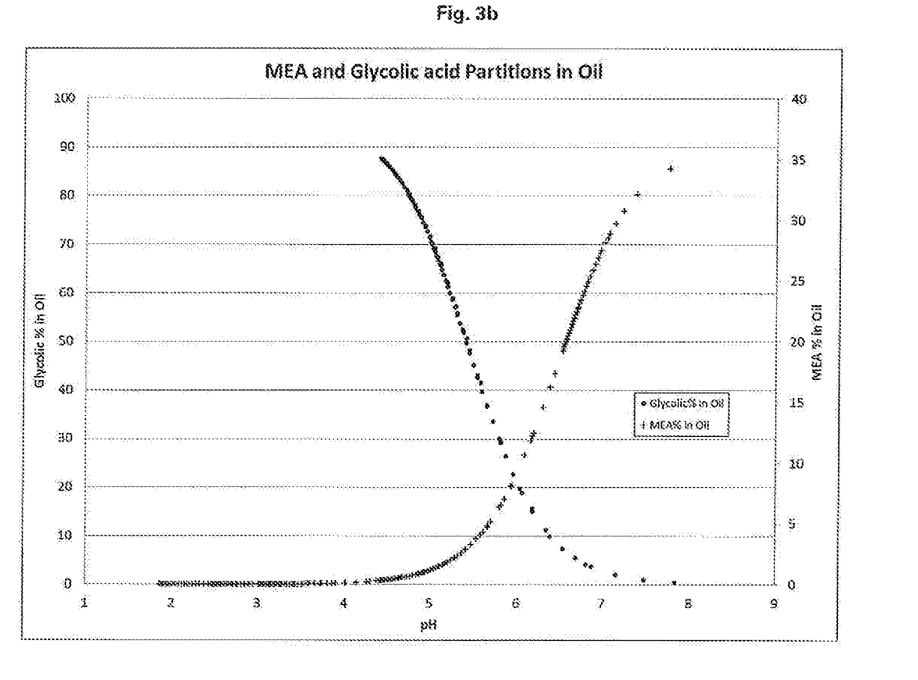
Figure 3C:
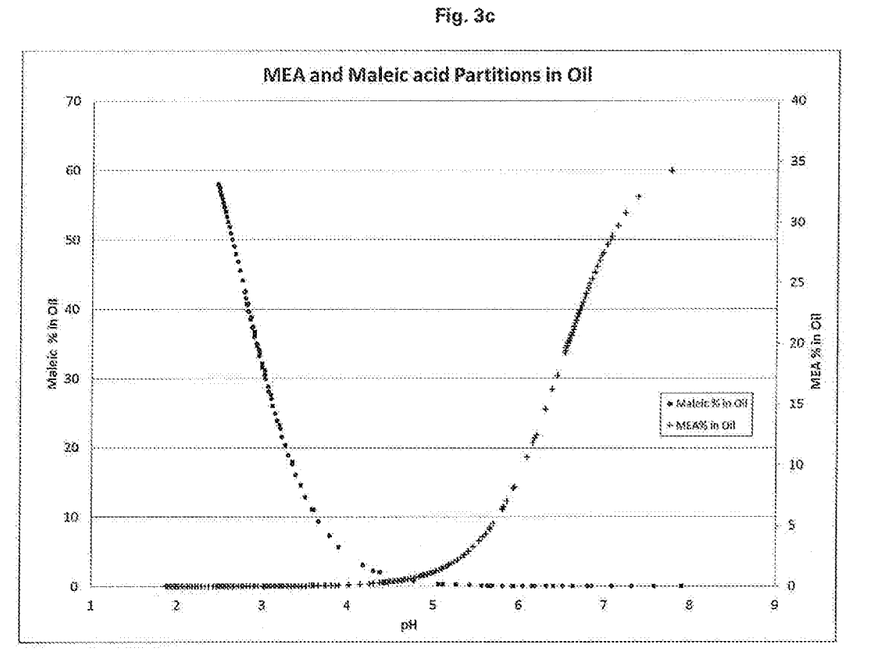
Figure 3D:
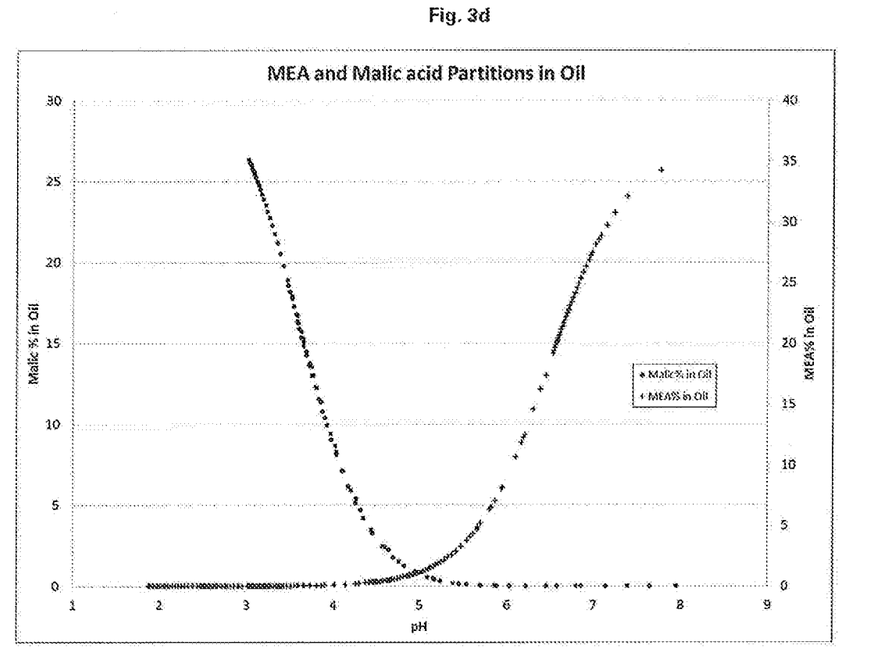
Figure 3E:
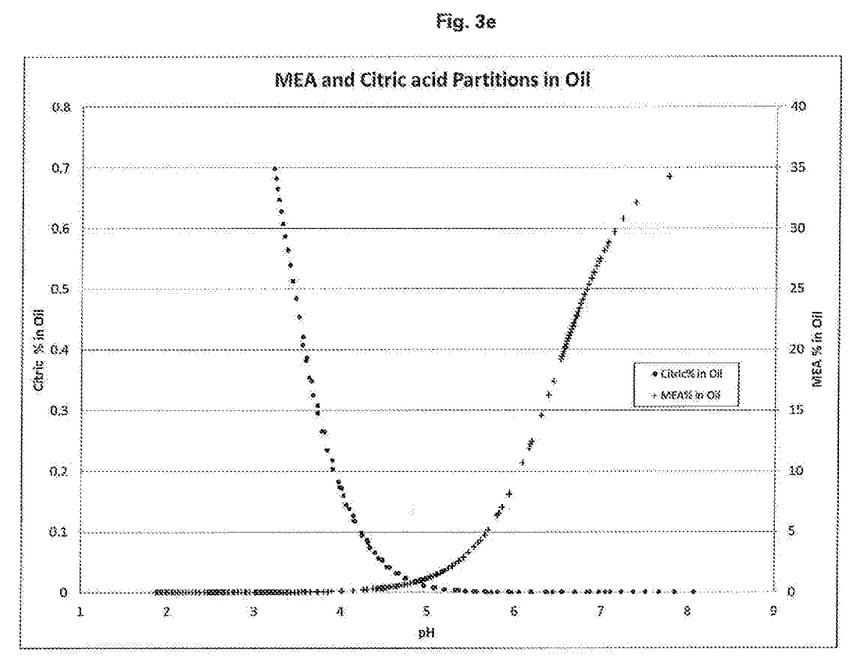
Figure 3F:
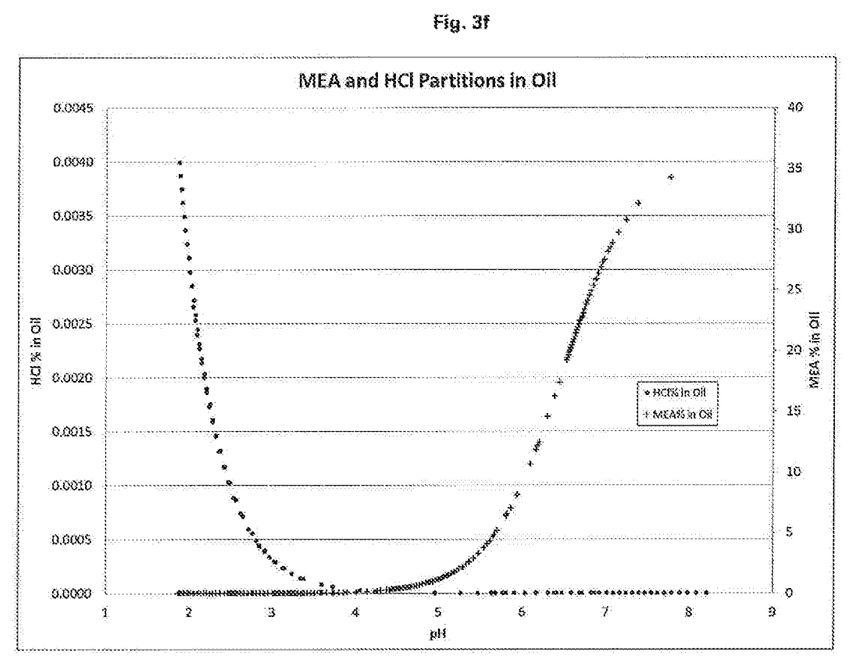

Example 1: Correlating Partitioning Levels of Amine Contaminants with Process pH Partitioning levels for the amines monomethylamine (MMA), monoethanolamine (MEA) and ammonia ($NH_3$) were measured across a range of pH levels at process conditions. A number of different acids were used to control the pH in the experiments. Further additives were also introduced into the system (such as further bases and metal salts) to investigate whether the presence of different types of additive may have an effect on the correlation between amine partitioning levels and process pH. Graphs depicting the correlations are shown in FIGS. 1a-c.

It can be seen that there is a strong correlation between amine partitioning level and the pH of the aqueous phase at process conditions, with higher partitioning levels observed at lower aqueous phase pH. It can also be seen that the correlation is substantially independent of the acid, or mixture of acids, being used. Furthermore, the correlation is not impacted by the presence of further additives. These results indicate that amine partitioning levels strongly correlate with the pH of the aqueous phase under process conditions, regardless of the mixture of additives that are present in a system.

Example 2: Correlating Partitioning Levels of Acids of Interest with Process pH Partitioning levels for the acids acetic acid (AcOH), hydrochloric acid (HC), citric acid, glycolic acid, malic acid, maleic acid, and $H_2S$ were measured across a range of pH levels. A number of different bases were used to control the pH in the experiments. Further additives were also introduced into the system (such as further acids and metal salts) to investigate whether the presence of different types of additive may have an effect on the correlation between acid partitioning levels and process pH. Graphs depicting the correlations are shown in FIGS. 2a-g.

A strong correlation between acid partitioning levels and the pH of the aqueous phase at process conditions was observed, with lower partitioning levels observed at lower aqueous phase pH. As with amine contaminants, the results indicate that the inclusion of further additives in the system does not impact on the correlation.

Example 3: Selecting Acidic Conditions for Use in a Partitioning Process

Correlations between the partitioning levels and the pH of the aqueous phase for monoethanolamine were plotted against correlations between the partitioning levels and the pH of the aqueous phase for six different acids of interest: acetic acid, glycolic acid, maleic acid, malic acid, citric acid and hydrochloric acid. Graphs depicting the correlations are shown in FIGS. 3a-f.

It can be seen from the graphs that approximately 99% of monoethanolamine was partitioned into the aqueous phase at pH levels of 5 or below. However, only some of the acids of interests achieve a partitioning level of greater 80% into the aqueous phase at pH levels of 5 or below. For instance, it can be seen from FIG. 3a that approximately 70% of the acetic acid remained in the non-aqueous phase at pH levels of 5 or below. This level of acid in the non-aqueous phase is clearly undesirable, since it will lead to corrosion downstream in a refinery. Accordingly, acetic acid was not selected for use in the partitioning process. For similar reasons, glycolic acid was also not selected (see FIG. 3b).

Each of the other acids exhibited a high level of partitioning into the aqueous phase (approximately 99%) at a pH of 5. However, hydrochloric acid was not selected for use in the partitioning process due to its relatively corrosive nature. Accordingly, an acidic environment was selected in which at least one of maleic acid, malic acid and citric acid were used.

Example 4: Effect of Temperature on the pH of an Aqueous Phase

The effect of temperature on the pH of an aqueous phase was investigated. Monomethylamine and monoethanolamine were acidified to an ambient conditions pH of 5.5 and 6, respectively, using a variety of different acids. Change in pH with temperature was then measured. The results are shown in FIGS. 4a-b.

Figure 4A:
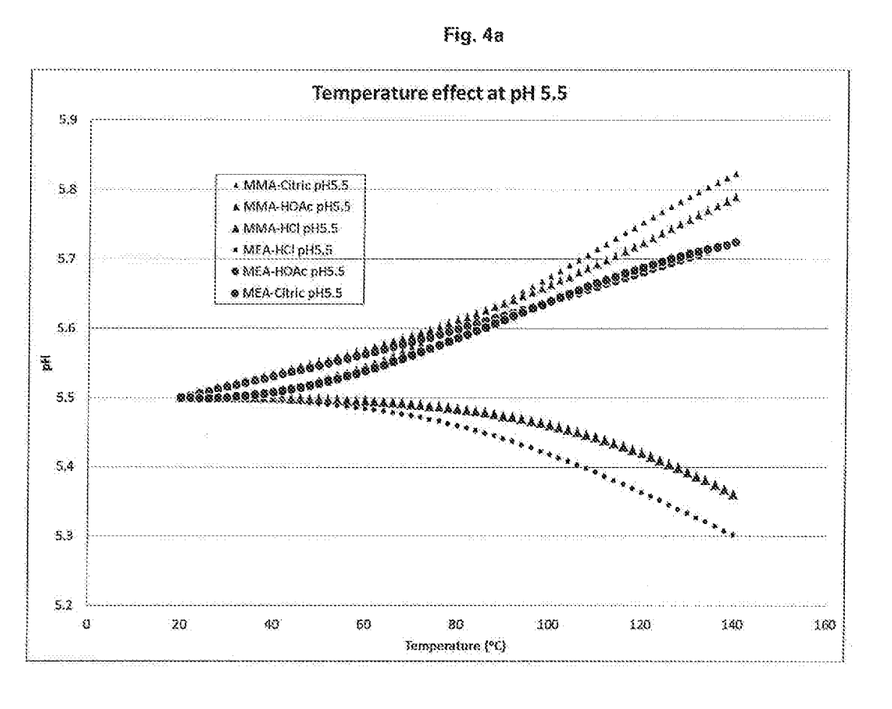
FIGS. 4a-b are graphs depicting the effect of temperature on the pH of aqueous phases acidified using different acids.
Figure 4B:
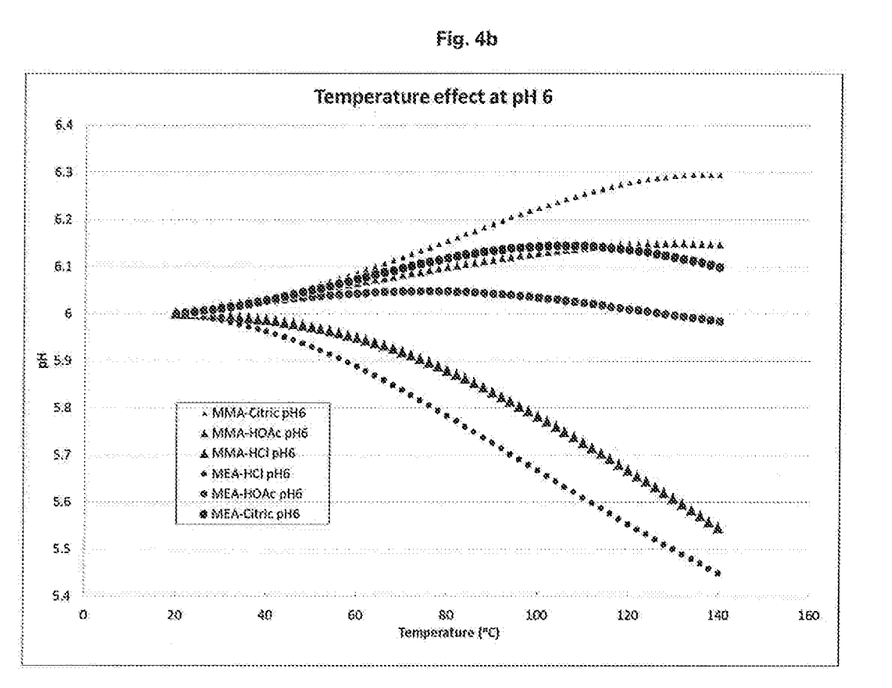

It can be seen that from FIG. 4a that the pH for the monoethanolamine aqueous phase can vary from 5.3 to 5.8 at 135° C. depending on the acid used, even though the pH at ambient condition is the same for all acids. An even larger range of pH levels, i.e. from 5.4 to 6.3, is observed for the monoethanolamine system (see FIG. 4b). These results demonstrate the significant effect that temperature may have on the pH of the aqueous phase.

Example 5: Correlating Partitioning Levels of an Amine Contaminant with pH as Measured Under Ambient Conditions and Process Conditions Partitioning levels for monoethanolamine with a number of different acids were measured under process conditions and correlated against the pH of the aqueous phase measured under ambient conditions. A graph of the results is shown in FIG. 5a.

Figure 5A:
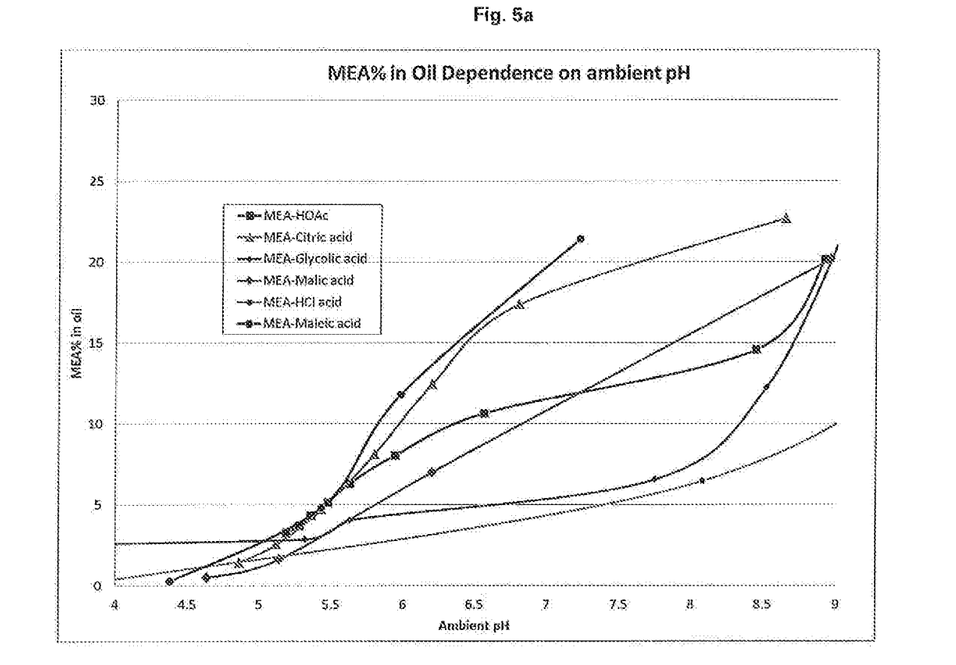
FIGS. 5a-b are graphs depicting the correlation between partitioning levels of monoethanolamine with aqueous pH measured under ambient conditions and under process conditions.

It can be seen from FIG. 5a that there is no direct correlation between monoethanolamine partitioning level and ambient pH. Indeed, any correlation varies greatly based on the acid that is used in the system. For example, at an ambient pH of 6.0, the amount of monoethanolamine that is still present in the oil can vary from 2.5% (when hydrochloric acid is used in the system) to 12.5% (when maleic acid is used).

Figure 5B:
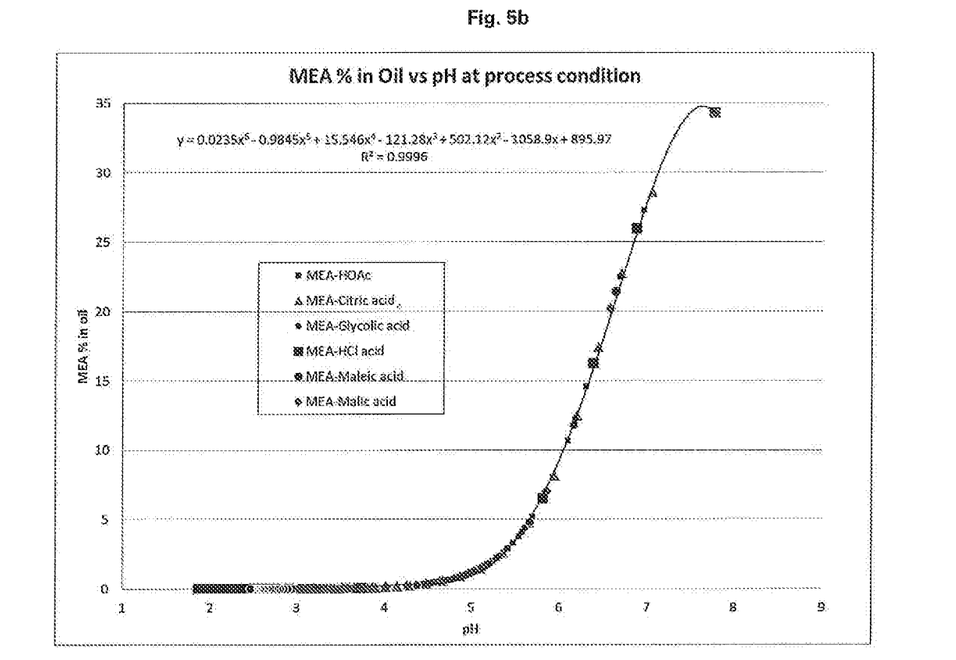

For comparison, FIG. 5b shows the strong correlation that is observed between partitioning level of monoethanolamine and process pH, irrespective of the acid that is used in the system. The partitioning level (%) into the aqueous phase has been expressed in terms of the formula $ax^6+bx^5+cx^4+dx^3+ex^2+fx+g$, where x is the pH of the aqueous phase.

The invention claimed is:

1. A method of removing contaminants from crude oil comprising:
    (a) mixing a hydrocarbon fluid and wash-water to wash the crude oil to remove a basic contaminant or an acid of interest;
    (b) introducing washed hydrocarbon fluid and wash-water of step (a) into a desalter via an inlet;
    (c) separating washed hydrocarbon fluid of step (b) from the wash-water by the formation of a non-aqueous phase comprising the washed hydrocarbon fluid and an aqueous phase comprising the wash-water;
    (d) removing the non-aqueous phase from the desalter via a hydrocarbon outlet;
    (e) removing the aqueous from the desalter via an aqueous outlet; and
    (f) correlating—in a system which comprises the basic contaminant, the non-aqueous phase, and the aqueous phase—a partitioning level of the basic contaminant into the aqueous phase with the pH of the aqueous phase; or
    correlating—in a system which comprises the acid of interest, the non—aqueous phase, and the aqueous phase—a partitioning level of the acid of interest into the aqueous phase with the pH of the aqueous phase; wherein the partitioning levels of the basic contaminant and the acid of interest, as well as the pH of the aqueous phase, have been obtained under conditions which are representative of those used in a partitioning process in which a basic contaminant is removed from a hydrocarbon fluid.

2. The method of claim 1, wherein the method comprises:
    (a) correlating the partitioning level of the basic contaminant into the aqueous phase with the pH of the aqueous phase; and
    (b) correlating the partitioning level of the acid of interest into the aqueous phase with the pH of the aqueous phase.

3. The method of claim 1, wherein the basic contaminant is selected from ammonia, an organic amine and a salt, and combinations thereof.

4. The method of claim 1, wherein the acid of interest is selected from hydrochloric acid, acetic acid, glycolic acid, citric acid, malic acid, maleic acid, hydrogen sulfide, carbon dioxide, and mixtures thereof.

5. The method of claim 1, wherein the hydrocarbon fluid used in the system is a refinery feedstock.

6. The method of claim 1, wherein the system which comprises the basic contaminant and the system which comprises the acid of interest comprise water in an amount of from 0.5 to 20% by weight of the system.

7. The method of claim 1, wherein the method comprises obtaining partitioning levels at a plurality of pH levels under conditions which are representative of those used in the partitioning process.

8. The method of claim 7, wherein the partitioning levels have been obtained at greater than 4 pH levels.

9. The method of claim 7, wherein the partitioning levels and the pH of the aqueous phase have been obtained at one or more of: a temperature which is representative of that used in the partitioning process, and a pressure which is representative of that used in the partitioning process.

10. A method for selecting an acidic environment for use in a partitioning process in which a basic contaminant is removed from a hydrocarbon fluid, said method comprising:
    (a) mixing a hydrocarbon fluid and wash-water to wash the crude oil to remove a basic contaminant or an acid of interest;
    (b) introducing washed hydrocarbon fluid and wash-water of step (a) into a desalter via an inlet;
    (c) separating washed hydrocarbon fluid of step (b) from the wash-water by the formation of a non-aqueous phase comprising the washed hydrocarbon fluid and an aqueous phase comprising the wash-water;
    (d) removing the non-aqueous phase from the desalter via a hydrocarbon outlet;
    (e) removing the aqueous from the desalter via an aqueous outlet;
    (f) correlating—in a system which comprises the basic contaminant, the non-aqueous phase, and the aqueous phase—a partitioning level of the basic contaminant into the aqueous phase with the pH of the aqueous phase; and/or
    correlating—in a system which comprises the acid of interest, the non—aqueous phase, and the aqueous phase—a partitioning level of the acid of interest into the aqueous phase with the pH of the aqueous phase; wherein the partitioning levels of the basic contaminant and the acid of interest, as well as the pH of the aqueous phase, have been obtained under conditions which are representative of those used in a partitioning process in which a basic contaminant is removed from a hydrocarbon fluid; and
    (g) selecting an acidic environment for use in the partitioning process based on correlations determined in step (f).

11. The method of claim 10, wherein the step of selecting an acidic environment comprises selecting a pH for the aqueous phase that is present in the partitioning process.

12. The method of claim 10, wherein the method comprises selecting an acidic environment which correlates with at least one of: a target level of basic contaminant partitioning into the aqueous phase, and a target level of acid of interest partitioning into the aqueous phase.

13. The method of claim 10, wherein the method comprises repeating step (g) for a plurality of acids of interest, and the step of selecting an acidic environment comprises selecting an acid from the plurality of interest for use in the partitioning process.

14. A method for controlling a partitioning process in which a basic contaminant is removed from a hydrocarbon fluid, said method comprising:
    (i) an acidic environment using the method of claim 10; and
    (ii) operating the partitioning process with the acidic environment selected in (i).

15. The method of claim 14, wherein step (i) comprises selecting a pH for the aqueous phase that is present in the partitioning process, and the method further comprises monitoring the pH of the aqueous phase in the partitioning process at process conditions, and maintaining the pH of the aqueous phase at the selected pH.

16. The method of claim 15, wherein the pH of the aqueous phase is maintained at the selected pH by modifying the amount of acid, base, $H_2S$ scavengers, calcium removal agents or neutraliser that is introduced into the partitioning process.

17. The method of claim 15, wherein a closed-loop control system is used for monitoring and maintaining the pH of the aqueous phase.

18. A method for estimating corrosion risk downstream of a partitioning process in which a basic contaminant is removed from a hydrocarbon fluid, said method comprising estimating the corrosion risk based on correlations determined using the method of claim 1.

19. The method of claim 1 further comprising the step of creating a database comprising:

(a) a correlation—in the system which comprises the basic contaminant, the non-aqueous phase comprising the hydrocarbon fluid, and the aqueous phase—between the partitioning level of the basic contaminant into the aqueous phase with the pH of the aqueous phase; or (b) a correlation—in the system which comprises the acid of interest, the non-aqueous phase comprising the hydrocarbon fluid, and the aqueous phase—between the partitioning level of the acid of interest into the aqueous phase with the pH of the aqueous phase;

wherein the partitioning levels of the basic contaminant and the acid of interest, as well as the pH of the aqueous phase, have been obtained under conditions which are representative of those used in a partitioning process in which a basic contaminant is removed from a hydrocarbon fluid.

\* \* \* \* \*